(12) United States Patent
Cerdà Baró et al.

(10) Patent No.: US 9,090,548 B2
(45) Date of Patent: Jul. 28, 2015

(54) CARBOXYLATE ACIDIFICATION

(71) Applicant: PURAC BIOCHEM B.V., Gorinchem (NL)

(72) Inventors: Agustin Cerdà Baró, Barcelona (ES); Jan Van Breugel, Woudrichem (NL); Willem Jacob Groot, Dordrecht (NL); André Banier De Haan, Best (NL); Peter Paul Jansen, Oss (NL)

(73) Assignee: PURAC BIOCHEM B.V., Gorinchem (NL)

( * ) Notice: Subject to any disclaimer, the term of this patent is extended or adjusted under 35 U.S.C. 154(b) by 0 days.

(21) Appl. No.: 14/376,639

(22) PCT Filed: Feb. 8, 2013

(86) PCT No.: PCT/EP2013/052525
§ 371 (c)(1),
(2) Date: Aug. 5, 2014

(87) PCT Pub. No.: WO2013/117687
PCT Pub. Date: Aug. 15, 2013

(65) Prior Publication Data
US 2015/0044741 A1 Feb. 12, 2015

Related U.S. Application Data (60) Provisional application No. 61/596,279, filed on Feb. 8, 2012.

(30) Foreign Application Priority Data

Feb. 8, 2012 (EP) ..................................... 12154534

(51) Int. Cl.
*C07C 51/02* (2006.01)
*C07C 59/08* (2006.01)
*C07C 53/122* (2006.01)
*C07C 55/10* (2006.01)
*C07C 55/14* (2006.01)
*C07C 57/04* (2006.01)
*C07C 57/13* (2006.01)
*C07C 57/15* (2006.01)
*C12P 7/56* (2006.01)

(52) U.S. Cl.
CPC ................. *C07C 51/02* (2013.01); *C07C 59/08* (2013.01); *C12P 7/56* (2013.01)

(58) Field of Classification Search
CPC ...... C07C 51/02; C07C 59/08; C07C 53/122; C07C 55/10; C07C 55/14; C07C 57/04; C07C 57/13; C07C 57/15; C12P 7/56
See application file for complete search history.

(56) References Cited

FOREIGN PATENT DOCUMENTS

CN 101748161 A 6/2010
WO WO 00/17378 A2 3/2000

OTHER PUBLICATIONS

International Search Report issued in International Patent Application No. PCT/EP2013/052525 dated May 29, 2013.
Written Opinion issued in International Patent Application No. PCT/EP2013/052525 dated May 29, 2013.
English-language translation of CN 101748161A, published Jun. 23, 2010.

*Primary Examiner* — Sun Jae Yoo
(74) *Attorney, Agent, or Firm* — Oliff PLC (57) ABSTRACT

A method for preparing a carboxylic acid by acidification of a liquid feed including a carboxylate salt, which method includes the steps of providing a liquid feed including magnesium carboxylate; providing a gas feed including gaseous hydrogen chloride; and acidifying the carboxylate to carboxylic acid by bringing the liquid feed into contact with the gas feed, thereby forming a liquid effluent including carboxylic acid and magnesium chloride, wherein the gas feed including gaseous hydrogen chloride is derived from a thermal decomposition step wherein an aqueous liquid including magnesium chloride is subjected to a temperature of at least 300° C., thereby decomposing magnesium chloride into magnesium oxide and hydrogen chloride, thus obtaining a solid including magnesium oxide and a gas comprising gaseous hydrogen chloride.

15 Claims, 3 Drawing Sheets

CARBOXYLATE ACIDIFICATION

The invention is directed to a method for preparing a carboxylic acid by acidification of a liquid feed comprising magnesium carboxylate with an acid.

Carboxylic acids, such as lactic acid and succinic acid, can be manufactured via fermentation of a carbon source, such as carbohydrates or glycerol, by micro-organisms. In such a fermentation process a carbohydrate source is typically fermented by means of a micro-organism to form a carboxylic acid. The liquid wherein the carbohydrate source is fermented is called the fermentation broth or the fermentation medium. The formation of carboxylic acid during fermentation will result in a decrease of the pH of the fermentation broth. Since such a decrease in pH can damage the micro-organism's metabolic process, it is common practice to add a neutralizing agent, i.e. a base, in the fermentation media in order to neutralize the pH or to maintain a optimum pH value for microorganism. As a result, carboxylic acid produced in the fermentation media is typically present in the form of a carboxylate salt. Although there are micro-organisms that are to some extent resistant to acidic environments, such that fermentation can be conducted at a low pH (e.g. at a pH of 3), even in these processes at least part of the carboxylic acid is obtained as a carboxylate salt.

To recover the carboxylic acid from the fermentation broth after fermentation, downstream processing is required. In such processing, the carboxylate salt in the fermentation broth needs to be converted into carboxylic acid. This can be achieved by reacting the carboxylate salt with an acid, resulting in carboxylic acid and a salt. Acidulation of carboxylate salts can be conducted with various acids such as sulphuric acid and hydrochloric acid (also sometimes referred to as an aqueous solution of hydrogen chloride).

WO00/17378 describes a process for the manufacturing of lactic acid, wherein a magnesium lactate solution is manufactured through a fermentation process. The solution is acidified with a solution of hydrogen chloride, to form a solution comprising lactic acid and magnesium chloride. This solution is subjected to a concentration step, the lactic acid is removed from the solution by extraction, and the resulting magnesium chloride solution is subjected to a thermal decomposition step, generating solid magnesium oxide and a gas stream comprising HCl and water. The gas stream comprising HCl and water is subsequently absorbed in water, to form an aqueous HCl solution of about 20 wt. %, which is recycled to the acidification step. The magnesium oxide may be provided to the fermentation step.

While the process of WO00/17378 is attractive in theory because it allows recycle of the magnesium chloride compounds, it has a number of disadvantages for commercial operation. A very important disadvantage is that the concentration of HCl in the aqueous solution will always be relatively low. When absorbing gaseous hydrogen chloride in water, the resulting HCl solution will be an azeotrope (water/HCl azeotrope). As a result, the HCl concentration obtained in such an aqueous HCl solution cannot be higher than the HCl concentration of the azeotrope of HCl and water, which is about 20 wt. % at room temperature. As the skilled person is aware, the azeotrope of HCl and water is temperature dependent. The azeotrope of HCl and water comprises 21.8 wt. % HCl at 81° C., 20.2 wt. % HCl at 109° C. and 19.7 wt. % HCl at 116° C. Therewith, unless additional measures such as azeotropic or extractive distillation are carried out, the concentration of the HCl solution is limited to about 20 wt. %. Said additional measures would require both expensive equipment and a significant amount of energy, and are therefore undesirable.

The upper limit of the HCl concentration of 20 wt. % means that in an acidification reaction of a magnesium carboxylate solution for each gram of effective HCl, 4 grams of water are added to the system. The presence of such large amounts of water is disadvantageous for a number of reasons. In the first place, it leads to a low acid concentration, which hampers recovery of the acid, therewith decreasing acid yield. Further, the remaining magnesium chloride solution also has a relatively low concentration, which means that when this solution is provided to a thermal decomposition step, a large amount of water has to be evaporated, either in the thermal decomposition step itself or in a preceding concentration step. Additionally, a larger volume of water in the extraction step of WO00/17378 leads to a larger amount of organic extractant ending up in the water phase, which is undesirable in view of the subsequent thermal decomposition step, and in view of extractant losses.

There is therefore need for a process which shows the advantageous recycle of magnesium chloride of the process of WO00/17378, without suffering the disadvantages thereof. The present invention provides such a process.

The present invention is directed to a method for preparing a carboxylic acid by acidification of a liquid feed comprising a carboxylate salt, which method comprises the steps of
  providing a liquid feed comprising magnesium carboxylate;
  providing a gas feed comprising gaseous hydrogen chloride; and
  acidifying the carboxylate to carboxylic acid by bringing the liquid feed into contact with the gas feed, thereby forming a liquid effluent comprising carboxylic acid and magnesium chloride,
wherein the gas feed comprising gaseous hydrogen chloride is derived from a thermal decomposition step wherein an aqueous liquid comprising magnesium chloride is subjected to a temperature of at least 300° C., thereby decomposing magnesium chloride into magnesium oxide and hydrogen chloride, thus obtaining a solid comprising magnesium oxide and a gas comprising gaseous hydrogen chloride.

In this method, the combination of a thermal decomposition step and the provision of a gas stream comprising gaseous HCl to a liquid feed comprising magnesium carboxylate makes for a method which is efficient as regards use of apparatus and recourses, and which allows addition of acid while limiting dilution of the liquid comprising magnesium carboxylate. Further advantages of the present invention and specific embodiments thereof will become clear from the further specification.

It has surprisingly been found that by conducting the acidification using gaseous HCl derived from the thermal decomposition step, an increased amount of HCl is adsorbed by the liquid feed comprising magnesium carboxylate than would be done by an equivalent amount of water. Not wishing to be bound by theory, it is believed that the amount of HCl that can be absorbed by the liquid feed is increased by the reaction of HCl with the carboxylate salt. Thus, the method of the invention effectively breaks the water/HCl azeotrope without expensive equipment or expending significant energy. By bringing the liquid feed into contact with the gas feed, gaseous hydrogen chloride will be absorbed by the liquid feed. while the addition of large amounts of water can be prevented, resulting in a decrease in dilution of the acidified solution. In particular, the amount of water added during acidification is reduced compared to using an aqueous HCl feed. Since a less diluted liquid effluent is obtained, a smaller amount of water will need to be evaporated to obtain a suitably high carboxylic acid concentration, resulting in reduced costs for evaporation. Further, subsequent purification steps can be conducted much more efficiently and in much smaller equipment when less water is present. Further, the magnesium chloride solution that is generated also has a higher concentration, making processing thereof more efficient.

That the process according to the invention in fact works is in itself surprising, because gas streams derived from the thermal decomposition of magnesium chloride in themselves generally contain gaseous water, originating, e.g., from the solution provided to the thermal decomposition step. It would therefore be expected that when the gas stream comprising gaseous HCl and water is provided to the liquid feed comprising magnesium carboxylate both the acid and the water present in the gas stream would be absorbed in the liquid feed, leading to a substantial dilution. However, due to the selective adsorption of HCl describe above, the amount of water absorbed in the system is lower than expected. Therefore, as compared to the process described in WO00/17378 where the gas stream is absorbed in water, which is subsequently provided to the acidification step, the process according to the invention shows an unexpected reduction in the amount of water provided to the acidification reaction. Additionally, as is evident to the skilled person, the process according to the invention makes use of less apparatus, which reduces associated costs.

The process according to the invention starts out with the provision of a liquid feed comprising magnesium carboxylate. The term "carboxylate" as used herein refers to the conjugate base of a carboxylic acid, which generally can be represented by the formula RCOO⁻. The term "carboxylic acid corresponding with the carboxylate" refers to the carboxylic acid that can be obtained by acidifying the carboxylate. It may therefore also be referred to as acidified carboxylate. The carboxylic acid corresponding with the carboxylate can generally be represented by the formula RCOOH.

The liquid feed may be an aqueous solution or an aqueous suspension (e.g. a slurry). The presence of solid matter in the aqueous feed is possible to a certain extent, dependent on the equipment used and the pumpability of the liquid fed (i.e. solid matter must not prevent the liquid feed from being pumped into the absorption unit), as known to the skilled person. Examples of solid matter that can be present in such a suspension are carboxylic acid in solid form and/or magnesium carboxylate in solid form. For processability reasons it is preferred for the liquid feed to be an aqueous solution.

The concentration of magnesium carboxylate in the liquid feed is not crucial and is typically 50-750 g/L. In case the liquid feed originates from a fermentation process, a concentration less than 50 g/L is not preferred. Values over 750 g/L may be undesirable, because the liquid feed may in this case become too viscous and/or contain too much solid matter to be sufficiently pumpable.

The liquid feed may, besides magnesium carboxylate, also comprise certain amounts of carboxylic acid, for example because it originates from a fermentation step conducted at low pH.

The liquid feed comprises magnesium carboxylate. The carboxylate is preferably a mono-, di- or tri-carboxylate comprising at least 2 to 8 carbon atoms (C2-C8 carboxylates) but the present invention is also suited for the longer carboxylates with more than 8 carbon atoms. The C2-C8 carboxylates may be selected from the group consisting of lactate, succinate, propionate, 3-hydroxypropionate, hydroxybutyrate, citrate, fumarate, itaconate, adipate, acrylate, levulinate, maleate, terephtalate and 2,5-furandicarboxylate. Preferably, the carboxylic acid is selected from the group consisting of lactate, succinate, 2,5-furandicarboxylate, propionate and 3-hydroxypropionate. In particular, good results have been obtained by using lactate and succinate. Higher magnesium carboxylates that also may very well be acidulated with the method according to the present invention can be for example the magnesium salts of a fatty acid (fatty acylate) and/or the magnesium salts of a mono- and/or di-lactylate (a lactylate ester of a fatty acid). Said magnesium fatty acids salts and lactylate salts may be selected from the magnesium salt of a fatty acid or lactylate ester of caproic, caprylic, capric, lauric, myristic, palmitic, stearic and oleic acid and/or mixtures hereof.

Dependent on the solubility of the magnesium chloride and carboxylic acid formed after acidulation, the magnesium chloride may precipitate in the absorption device or unit before the carboxylic acid does. The magnesium chloride may then preferably be dissolved again before being fed to the thermohydrolysis reactor. For processability reasons it is preferred for the liquid feed to be an aqueous solution. If the carboxylate is chosen such that its corresponding carboxylic acid has a solubility lower than the solubility of magnesium chloride, in particular a solubility lower than 60 g/100 g water at 20° C. (more in particular lower than 30 g/100 g water, even more in particular lower than 15 g/100 g water) the carboxylic acid may precipitate before the magnesium chloride. The magnesium chloride solution may then be separated from the precipitated carboxylic acid, and, if so desired, directly be fed to the thermohydrolysis reactor. The term "solubility" as used hereinabove refers to the maximum weight amount of a compound that can be dissolved in a certain amount of water at 20° C.

The gas feed comprising gaseous hydrogen chloride is derived from a thermal decomposition step wherein an aqueous liquid comprising magnesium chloride is subjected to a temperature of at least 300° C., thereby decomposing magnesium chloride into magnesium oxide and hydrogen chloride, thus obtaining a solid comprising magnesium oxide and a gas comprising gaseous hydrogen chloride.

The gas feed provided to the acidification reaction generally comprises at least 1 wt. %, preferably at least 2 wt. %, more preferably at least 5 wt. % of hydrogen chloride, based on the total weight of the gas. A concentration of less than 1 wt. % is generally undesirable, because such a concentration requires the use of very large gas pipes to feed the gas feed to the liquid feed in order to maintain an efficient acidification. Although high concentrations of hydrogen chloride in the gas feed are generally desirable, the gas feed will in practice comprise 20 wt. % or less hydrogen chloride. A suitable concentration of HCl in the gas feed is 7-12 wt. %. The HCl concentration of a gas obtained in thermohydrolysis of magnesium chloride typically falls within this range, although concentration or dilution steps are possible should it for some reason be desired to work with higher or lower HCl concentrations.

Depending on the further composition of the gas, the gas feed generally comprises at least 25 wt. % of inert gas, in particular of inert gas selected from the group consisting of $N_2$, $CO_2$ and mixtures thereof (such as air). This may, e.g., result from the thermohydrolysis being conducted in the presence of inert gases, for example in the presence of air. The term "inert gas" as used herein refers to a gas that does not react, condense or absorb with the liquid feed during acidification and leaves the liquid feed as a gas after having been contacted with the liquid feed. The inert gas concentration may be higher, e.g., at least 50 wt. In one embodiment, the gas feed may comprise 40-80 wt. % nitrogen gas. The gas feed may comprise up to 95 wt. % inert gas. In one embodiment a gas feed obtained in $MgCl_2$ thermohydrolysis is used which comprises 40-50 wt. % $N_2$, 0-5 wt. % $O_2$ and 5-15 wt. % $CO_2$.

In one embodiment, the HCl-containing gas stream provided to the acidification reaction comprises gaseous water. As the HCl-containing gas stream derives from the thermal decomposition of a solution of magnesium chloride, the decomposition product stream will generally contain gaseous water in addition to gaseous HCl. While it is possible to remove water from the gas stream, it is a particular feature of the invention to provide the gas stream from the thermal decomposition step to the acidification step without intermediate water removal.

In one embodiment, the gas stream provided to the acidification reaction comprises gaseous water and gaseous HCl, wherein the hydrogen chloride to water weight ratio in the gas feed is between 1:10 and 1:0.1, e.g. between 1:6 and 1:3. In particular, the $HCl/H_2O$ ratio may be between 1:10 and 1:4, in particular between 1:6 and 1:4, more in particular between 1:5 and 1:4.

The gas stream provided to the acidification reactor may, e.g., comprise at least 5 wt. % of water, more in particular at least 10 wt. % of water, still more in particular at least 20 wt. % of water. As a maximum amount of water, a value of 90 wt. % may be mentioned. In one embodiment the amount of water is in the range of 25-50 wt. %. The amount of water in the gas stream in a particular case will depend, int. al., on the amount of water in the magnesium chloride solution and the amount of inert gas present during the thermal decomposition. In case of preparing the gas feed by thermally decomposing a magnesium chloride solution, the magnesium chloride solution preferably comprises 15-40 wt. %, more preferably 25-30 wt. % magnesium chloride. Too low $MgCl_2$ concentrations are not desirable due to the high energy costs involved in evaporating water during thermohydrolysis. In one embodiment, a gas feed obtained by thermohydrolysis of a 20-40 wt. % magnesium chloride solution will generally have a hydrogen chloride to water weight ratio ($HCl/H_2O$ ratio) that is at least 1:10 and at most 1:4. In case a magnesium chloride concentration of 25-30 wt. % is used, it will generally have a $HCl/H_2O$ ratio between 1:6 and 1:4, in particular between 1:5 and 1:4. In this case, the gas feed typically comprises 5-15 wt. % HCl and 30-45 wt. % water.

In general, the aqueous feed will have a temperature in the range of 20-150° C.

It has been found, however, that in a preferred embodiment of the invention, the temperature of the liquid feed is increased. It has been found that the use of an increased temperature leads to an increased selectivity for the adsorption of HCl from the gas stream as compared to the adsorption of water from the gas stream. More specifically, at increased temperature of the liquid feed, the gaseous HCl is still adsorbed to a large extent from the gas stream, while the adsorption or condensation of the water which is also present in the gas stream is reduced, even when the process is operated under atmospheric pressure. This means that when in the process according to the invention the temperature of the liquid feed is increased, the dilution of the liquid feed is prevented even further. Therefore, in one embodiment of the present invention the liquid feed which is contacted with the stream of gaseous acidification reaction has a temperature of at least 60° C., more in particular at least 75° C. Most preferably, the liquid feed has a temperature of 80-120° C.

The temperature of the gas feed is not particularly critical. It is preferably 20° C. or higher, more preferably higher than 75° C. Where the temperature of the gas feed is relatively low, e.g., below 20° C., or sometimes at 75° C. or lower, water that is present in the gas feed may condense in the liquid feed, also depending on the temperature of the liquid feed. Furthermore, the gas feed preferably has a temperature of 150° C. or less. Higher temperatures will require expensive equipment for conducting the absorption, e.g. made from highly acid/corrosion resistant and temperature resistant construction material. The gas feed may for example have a temperature of 80-120° C.

As will be discussed in more detail below, the thermal decomposition step takes place at a temperature of at least 300° C. In one embodiment the gas stream resulting from the thermal decomposition step is provided to a heat exchange step, wherein the temperature of the gas stream is decreased to a value in the range of 80-150° C., in particular 80-120° C. A gas stream with this temperature can be provided directly to the acidification step.

The temperature at which the acidification is conducted is mainly determined by the temperature of the carboxylate feed. The temperature of the gas feed has a relatively small effect on the acidification temperature compared to the temperature of the carboxylate feed.

In one embodiment, the temperature of the carboxylate feed is 1-50° C. higher than the temperature of the gas feed, more preferably 3-25° C., for example 5-15° C. Such a temperature difference may enhance the prevention of condensation of gaseous water in the region where the gas feed enters the absorption column.

The temperature at the acidification step takes place wherein the liquid feed is contacted with the gas feed is with the gas feed is preferably at least 60° C., more in particular at least 75° C. Most preferably, temperature at the acidification step takes place is in the range of 80-120° C.

As explained above, by selecting an appropriate temperature for the process according to the invention, in particular for the liquid magnesium carboxylate solution, it is possible to increase the selectivity for the adsorption for HCl from the gas stream as compared to the adsorption of water from the gas stream.

Depending on the amount of water in the gas stream and the selection of the temperature it may be preferred to select the temperature in such a manner that at least 50 wt. % of the gaseous water present in the gas feed is not condensed in the liquid feed, more preferably at least 75 wt. %, even more preferably at least 85 wt. %, while the adsorption of HCl from the gas stream is maintained. The part of the gaseous water that does not condense will leave the liquid feed as gaseous water. The amount of HCl adsorbed from the gas stream is generally at least 90% of the HCl present in the gas stream, more in particular at least 95%, still more in particular at least 99%.

The amount of HCl provided is also determined by the amount of carboxylate to be neutralised. In one embodiment acidulation is conducted using an excess of HCl. The excess is preferably small, such that the resulting product is not highly acidic, which may not be desirable in view of further processing such a solution.

The selectivity of the adsorption process for HCl from the gas stream as compared to the selectivity for water from the gas stream may also be influenced by the pressure in the absorption unit wherein the acidification is conducted. By decreasing the pressure of the absorption unit, and/or by increasing the temperature of the liquid feed as discussed above, the amount of water adsorbed may be reduced, while the amount of acid adsorbed is not reduced. (Near) atmospheric pressure is generally suitable, while a slight pressure reduction may also be attractive. Adsorption can, e.g., be carried out at a value of 0.5-2 bar, in particular 0.8-1 bar, e.g., 0.9-1 bar. It has been found that carrying out an acidification reaction at a temperature 80-120° C. under (near) atmospheric pressure is very suitable to enable a high selectivity for the adsorption of HCl from the gas stream as compared to the adsorption of water from said gas stream.

In one embodiment, the temperature and pressure of the process according to the invention are selected in such a manner that not only the selectivity for the adsorption for HCl from the gas stream as compared to the adsorption of water from the gas stream is increased, but also additional water is evaporated from the system, resulting in a further increase of the concentration.

Not wishing to be bound by theory, it is believed that an additional advantage of absorbing the gaseous hydrogen chloride in the liquid feed is that energy will be released in the liquid feed and/or the gas feed due to the absorption of HCl by water. The dissociation of HCl into H+ and Cl— is an exothermic reaction. The energy released as a result of the dissociation will heat up the liquid feed and therewith decrease the amount of water adsorbed into the liquid, as described above.

The following parameters play a role in determining the selectivity for the HCl adsorption as compared to water adsorption from the gaseous feed, and therewith the amount of water adsorbed during the acidification step: A higher temperature, a lower pressure, and higher HCl concentrations lead to a decrease in the amount of water adsorbed, and/or where applicable an increase in the amount of water evaporated. Lower temperatures, higher pressures, and lower HCl concentrations lead to an increase in the amount of water adsorbed, and/or where applicable a decrease in the amount of water evaporated.

Based on this information, the skilled person will understand how to manage the water balance during acidification and can adjust the amount of water entering or leaving the system to his needs. Although in general, it is desirable to obtain a liquid effluent that is highly concentrated, there may in certain embodiments be a limit due to undesirable precipitation of magnesium chloride.

The acidification can be conducted in any unit suitable for absorption of HCl in an aqueous liquid. Due to the acidic conditions of the acidification step, the unit is preferably made from acid-resistant material such as plastic or suitable duplex steel grades. The shape of the unit is not essential. The gas feed is, for example, fed to the unit at or near its bottom, while the liquid feed is fed to the column at or near its top. Examples of suitable absorption units are columns (e.g. packed columns, bubble columns), scrubbers (e.g. venture scrubbers), tray absorbers and stirred tanks. The person skilled in the art will know what suitable absorption unit to choose.

The product from the acidification step is an aqueous liquid, also indicated herein as liquid effluent, comprising dissolved magnesium chloride and carboxylic acid. The aqueous liquid may be a solution, slurry, suspension, or emulsion. The carboxylic acid may be at least partly in solid form, due to precipitation, but it may also be in liquid form.

In one embodiment the aqueous liquid generally has a magnesium chloride concentration in the range of 5 to 50 wt. %, in particular in the range of 10-40 wt. %, more in particular in the range of 20-35 wt. %.

In one embodiment the aqueous liquid comprises carboxylic acid in an amount in the range of 5 to 60 wt. %, preferably in the range of 10 to 50 wt %, more preferably in the range of 20-40 wt. %. The carboxylic acid may be present in the aqueous medium in dissolved form or in non-dissolved form, e.g., in the form of particles formed by precipitation or crystallisation. The form in which the carboxylic acid is present will depend on the nature of the acid.

The aqueous liquid effluent product can be processed in various manners, which will be discussed in more detail below.

In the process according to the invention, the gas feed comprising gaseous hydrogen chloride is derived from a thermal decomposition step wherein an aqueous liquid comprising magnesium chloride is subjected to a temperature of at least 300° C., thereby decomposing magnesium chloride into magnesium oxide and hydrogen chloride, thus obtaining a solid comprising magnesium oxide and a gas comprising gaseous hydrogen chloride.

Thermal decomposition of chlorides is commonly known from the steel industry, wherein iron(III)chloride ($FeCl_3$) is thermally decomposed into iron(II)oxide ($Fe_2O_3$) and chlorine gas ($Cl_2$). In this field, thermal decomposition of $MgCl_2$ to HCl and MgO is also known, for example known from GB 793,700. Suitable apparatuses for conducting thermal decomposition are known in the art. For example, a spray roaster or a fluid bed roaster can be used. Such apparatuses can for example be obtained at SMS Siemag.

Thermal decomposition is conducted at a temperature of a least 300° C., which is the minimum temperature at which $MgCl_2$ decomposes. Preferably, thermal decomposition is conducted at a temperature of at least 350° C., for example 350-450° C. Due to energy costs, the temperature is preferably below 1000° C., more preferably below 800° C. For example, the temperature at which thermal decomposition is conducted may be 350-600° C. Preferably, the magnesium chloride solution subjected to the thermal decomposition step has a $MgCl_2$ concentration of 15-40 wt. %, more preferably 25-35 wt. %. Too high amounts of magnesium chloride present in the solution may result in precipitation of magnesium chloride upon entering the thermohydrolysis unit.

The thermal decomposition step is carried out by methods known in the art, which require no further elucidation here.

The thermal decomposition step generates a gas stream comprising HCl and magnesium oxide. In one embodiment the gas stream resulting from the thermal decomposition step, which has a temperature in the range specified above, is provided to a heat exchange step, wherein the temperature of the gas stream is decreased to a value in the range of 80-150° C., in particular 80-120° C. A gas stream with this temperature can be provided directly to the acidification step.

The magnesium oxide (MgO) is typically obtained in the form of a powder. In one embodiment, the magnesium oxide is hydrated with water, e.g. by quenching the MgO with water, thereby forming a magnesium hydroxide ($Mg(OH)_2$) suspension. The magnesium hydroxide is preferably recycled for use in the fermentation process. For example, the $Mg(OH)_2$ may be used as a neutralizing agent in a fermentation process. Alternatively, the $Mg(OH)_2$ is first converted to magnesium carbonate ($MgCO_3$), which is then used as a neutralizing agent in a fermentation process.

The HCl obtained in the thermal decomposition step is recycled by using it in the acidification step as described in detail above.

The above-mentioned method steps may be part of a larger process, wherein the liquid effluent from the absorption unit is further processed and the magnesium chloride is processed in order to be made suitable for re-use or recycling.

Accordingly, the method of the invention may further comprise a separation step, wherein the carboxylic acid and magnesium chloride present in the liquid effluent are separated from each other, for example by isolating the carboxylic acid from the liquid effluent, such that a magnesium chloride solution remains. The separation step typically results in a carboxylic acid product stream and an aqueous liquid comprising magnesium chloride. Said aqueous liquid comprising magnesium chloride may be a suspension, but preferably is a solution, as a solution is better suitable for thermal decomposition in the thermohydrolysis reactor). Any method suitable for separating carboxylic acid from magnesium chloride may be used. For example, the carboxylic acid and magnesium chloride may be separated by precipitation, which technique is in more detail described below. In another embodiment, the carboxylic acid and magnesium chloride may be separated by means of extracting the carboxylic acid from the magnesium chloride solution. This method will also be described in more detail below. In a further embodiment the carboxylic acid and magnesium chloride are separated by other techniques than precipitation and/or extraction.

An advantage of the process according to the invention where it is followed by a separation step is that it may result in an increased yield of carboxylic acid. By using the acidification step of the invention, the liquid effluent will have an increased carboxylic acid concentration. Such an increased concentration will generally result in a more efficient separation and/or isolation of the carboxylic acid, thus leading to an increase in yield.

The combination of the acidification step and the thermohydrolysis step is particularly desirable with respect to the water balance in the method of the invention. When conducted as a continuous process, no water needs to be added in any of the steps described above, thus keeping the carboxylate solution as concentrated as possible. As described above, this not only saves energy due to no or less evaporation of water during the process, but may also increase the yield of the carboxylic acid.

For example, in case additional water would have been added to the liquid feed in the acidification step (e.g. by using a HCl solution), this additional water would have to be evaporated either during the thermal decomposition step or during a preceding concentration step, which would require extra energy.

Furthermore, by preventing dilution of the liquid effluent, the separation step will be more efficient such that no or only very small amounts of carboxylic acid will be present in the magnesium chloride solution. This is important, because any carboxylic acid remaining in the magnesium chloride solution will be incinerated and thus result in a decrease of the total yield of carboxylic acid. Additionally, where a separation method comprising extraction is used, the presence of a large amount of water will result in an increased amount of the extraction agent dissolving in the water phase, and therewith being provided to the thermal decomposition step, where it will be incinerated, leading to extractant loss.

The method of the invention is preferably a continuous process. Nevertheless, it may be conducted as a batch process.

The method may comprise a fermentation step, wherein a liquid feed comprising a carboxylate salt is formed. Such a step typically comprises the substeps of fermenting a carbon source by means of a micro-organism to form a fermentation medium comprising a carboxylic acid and (partially) neutralizing the fermentation medium in order to establish a desired pH by adding a neutralizing agent, preferably a magnesium base, to form the carboxylate salt. Subsequently, biomass may be separated from the fermentation medium, for example by (ultra)filtration, centrifugation or decantation of the biomass or by precipitation of the magnesium carboxylate from the fermentation medium. As described above, magnesium oxide obtained in the thermal decomposition step can be recycled in the fermentation step as a neutralizing agent or precursor thereof.

In one embodiment of the invention, especially where the fermentation yields a solution with a low carboxylate concentration, it may be preferred to carry out a concentration step between the fermentation step and the acidification step. A concentration step is generally associated with an increase in temperature of the liquid feed comprising magnesium carboxylate, and is therefore particularly attractive where it is desired to carry out the acidification step at increased temperature, e.g., at a temperature of at least 60C, as discussed above.

The method according to the invention is particularly suitable for integration with other process steps. Examples of processes comprising the steps of the method according to the invention are presented in the Figures.

Figure 1:
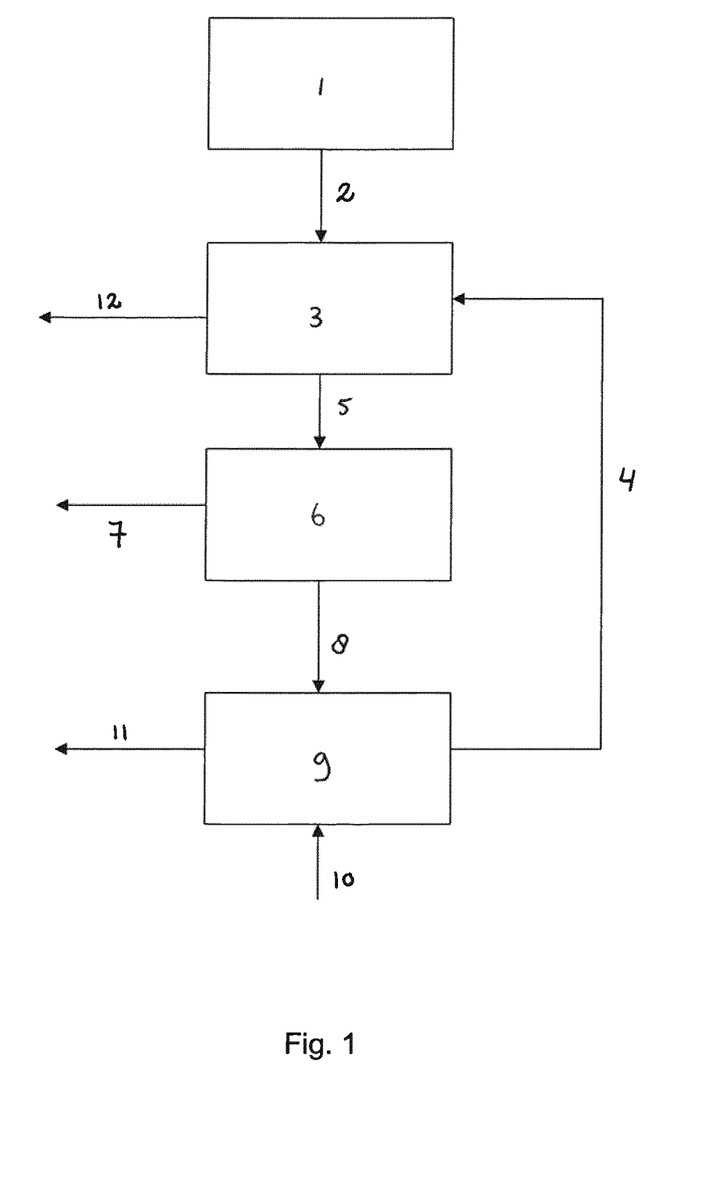

FIG. 1 illustrates one embodiment of the present invention. A fermentation process is carried out in fermentation reactor (1) generating a carboxylic acid. A magnesium base is added during fermentation (not shown), resulting in the formation of a magnesium carboxylate. A product stream (2) comprising magnesium carboxylate is withdrawn from the fermentation reactor, and provided to an acidification reactor. If so desired, intermediate purification steps such as biomass removal may be carried out in manners known in the art. A liquid feed comprising magnesium carboxylate is provided to acidification reactor (3), where it is contacted with a gas stream (4) derived from thermal decomposition step (9). In the acidification reactor (3) the magnesium carboxylate is converted to carboxylic acid and magnesium chloride by reaction with gaseous HCl. A stream comprising inert gas, and generally also gaseous H2O, is withdrawn through line (12). Stream (5) comprising carboxylic acid and magnesium chloride is subjected to a separation step (6). In the figure this is indicated as taking place in a separate reactor, but, depending on the separation method, this may also take place in the acidification reactor. The separation step (6) generates a stream (7) comprising carboxylic acid and a stream (8) which is an aqueous liquid comprising magnesium chloride. Stream (8) is provided to a thermal decomposition unit (9), where the magnesium chloride is converted to HCl and MgO with the addition of inert gas through line (10). The HCl-containing gas stream (4) is provided to the acidification reactor (3). The MgO, which is withdrawn through line (11) may, if so desired, be reacted with water to form a solution comprising magnesium hydroxide, which is recycled to the fermentation reactor (1).

Figure 2:
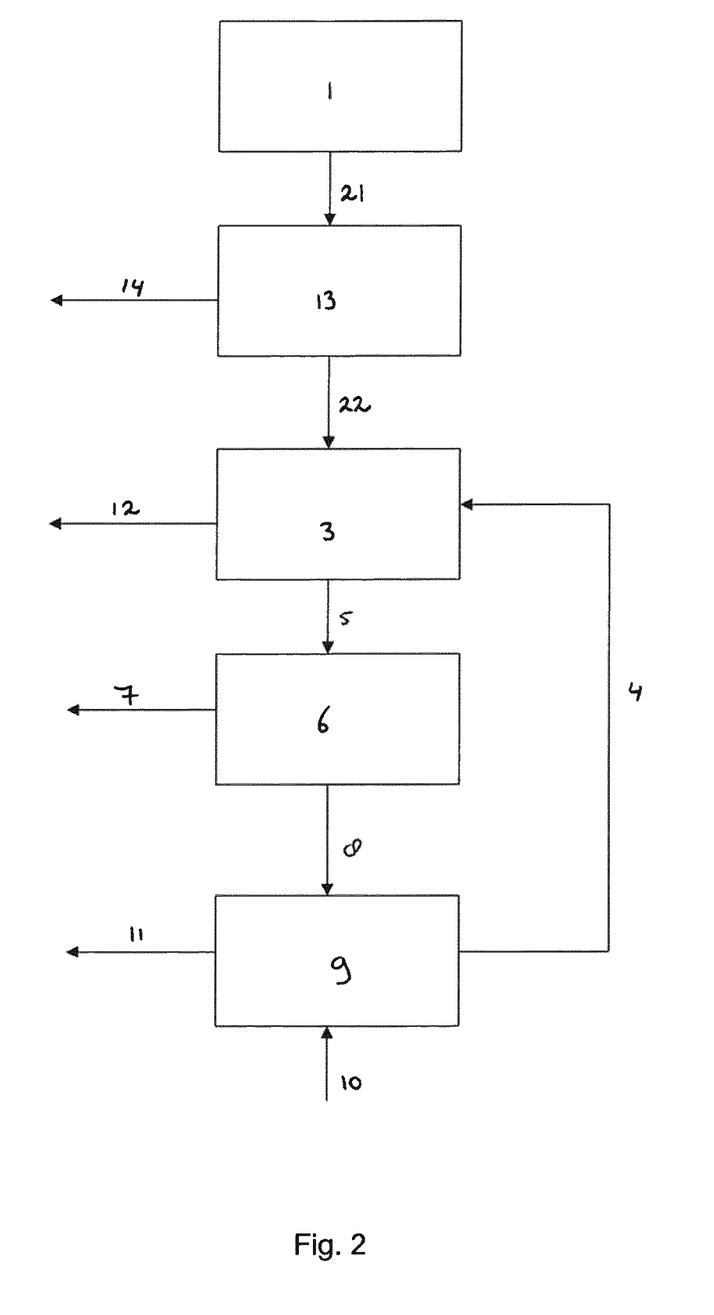

FIG. 2 shows a variation on the process of FIG. 1, wherein a concentration step (13) is inserted between fermentation step (1) and acidification step (3). A product stream (21) comprising magnesium carboxylate is withdrawn from the fermentation reactor (1), and provided to concentrator (13). Excess water is removed through line (14) and a concentrated product stream (22) is provided to acidification step (3). As has been discussed before, an attractive embodiment of the method according to the invention is one wherein a concentration step is carried out resulting in a concentrated liquid with a temperature of at least 60° C., in particular at least 75° C., more in particular in the range of 80-120° C., as this will lead to a high selectivity for the adsorption of HCl in the liquid feed as compared to the adsorption of water from the gas feed.

Figure 3:
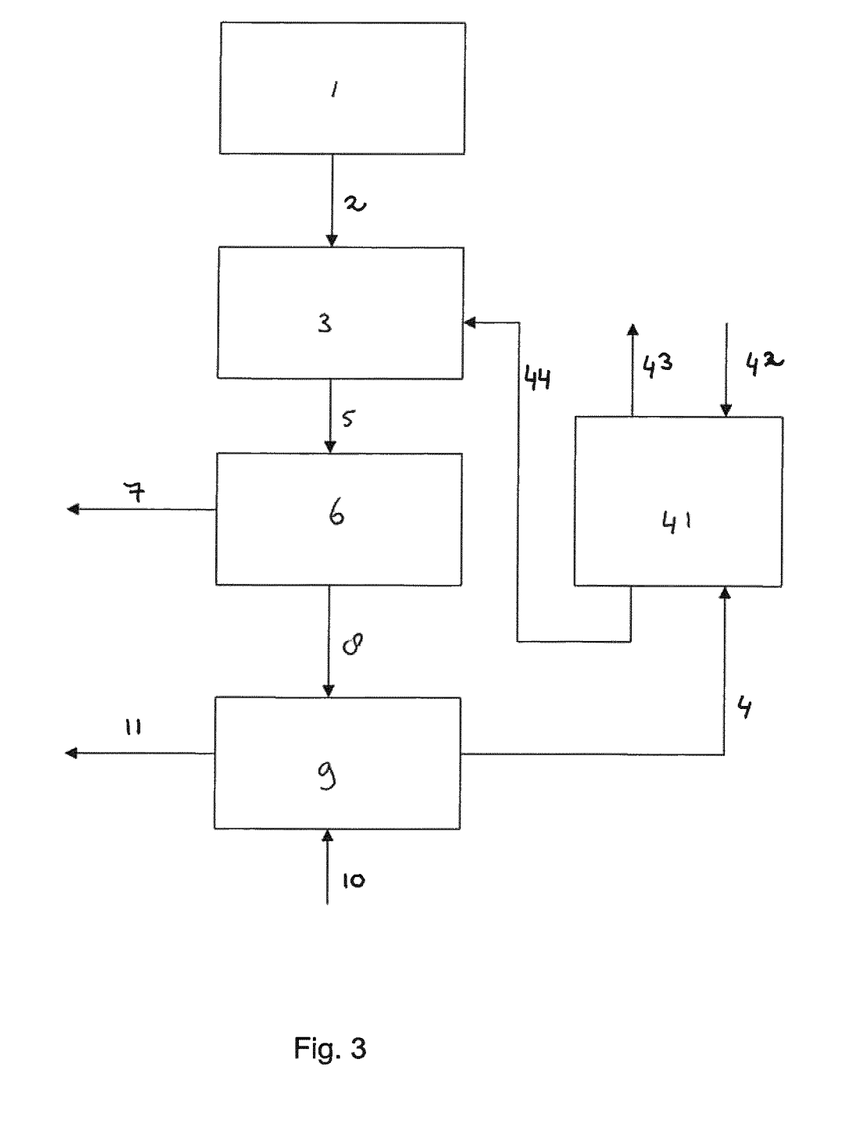

FIG. 3 illustrates a comparative process, wherein, as compared to the process according to the invention of FIG. 1, the gas feed withdrawn from the thermal decomposition step (9) through line (4) is not provided to the acidification step (3), but instead to a separate adsorption reactor (41), where it is contacted with water through line (42), resulting in an aqueous HCl solution, which is provided to the acidification reactor (3). Inert gas is withdrawn through line (43). This figure illustrates that, in addition to the other disadvantages of this comparative process, this process also requires the use of additional apparatus not required by the process according to the invention.

As indicated above, in one embodiment, the process according to the invention comprises the step of subjecting the liquid effluent comprising carboxylic acid and magnesium chloride to a separation step, to yield an aqueous liquid, in particular an aqueous solution, comprising magnesium chloride and carboxylic acid.

In one embodiment, the separation step is an extraction step, comprising extracting the carboxylic acid from the aqueous mixture into an organic liquid, thereby obtaining an organic carboxylic acid solution and an aqueous waste liquid comprising magnesium chloride. In a preferred embodiment, the carboxylic acid is subsequently extracted from the organic carboxylic acid solution into an aqueous liquid, thereby obtaining an aqueous carboxylic acid solution and a second organic liquid. Thus, in a preferred embodiment, the separation step encompasses forward extraction of the acid from the aqueous effluent into an organic liquid, followed by back extraction of the acid from the organic liquid into water, thus forming an aqueous solution of the carboxylic acid. It is also possible, however, not to carry out the back extraction step, but to isolate the acid from the organic liquid by other means, e.g., evaporation or distillation.

In one embodiment, the organic liquid used in the extraction step comprises an organic solvent selected from the group consisting of ketones and ethers. Preferably, the organic liquid comprises at least 90 wt. % of the organic solvent, preferably at least 95 wt. %, more preferably at least 99 wt. %. In one embodiment, the organic liquid is the organic solvent. Optionally, small amounts of water can be present in the first organic liquid, in particular when the liquid (partly) comprises recycled organic solvent from a recycle step after extraction.

It has been found that ketones and ethers are attractive in extraction process, because they show a high distribution ratio, resulting in a high acid yield. It is preferred to use ketones, in particular C5+ ketones, more in particular C5-C8 ketones in the present invention. C5+ stands for ketones with at least 5 carbon atoms. Mixtures may also be used. The use of C9+ ketones is less preferred, because these compounds are believed to result in more contaminants in the end product. The use of methyl-isobutyl-ketone (MIBK) has been found to be particularly attractive. Ketones are also preferred because they are stable under process conditions, in that they do not react or decompose to a substantial extent, thus giving rise to few contaminants, and allow a stable process operation. Ethers may also be used, in particular C3-C6 ethers. It has been found, however, that they are less preferred, in particular because the use of ethers results in more solvent loss and in more contaminants in the end product. Within de ether-group, the use of methyl tert-butyl ether (MTBE) and diethyl ether (DEE) may be preferred, but less preferred than the use of ketones.

In one embodiment of the present invention the carboxylic acid and magnesium chloride may be separated from each other after acidification of magnesium carboxylate with HCl, by precipitation. In this case, the method of the invention may further comprise the steps of optionally a concentration step, wherein the liquid effluent comprising carboxylic acid and $MgCl_2$ is concentrated;

precipitating the carboxylic acid from the solution comprising carboxylic acid and $MgCl_2$, thereby obtaining a carboxylic acid precipitate and a $MgCl_2$ solution, wherein the carboxylic acid corresponding with the carboxylate has a solubility in water at 20° C. of 60 g/100 g water or less and wherein the carboxylate is preferably succinate.

The method of the invention comprising these steps is hereinafter referred to as the precipitation method of the invention. The liquid feed is hereinafter referred to as the carboxylate solution or suspension. The liquid effluent is hereinafter referred to as the solution comprising the carboxylic acid and $MgCl_2$ (or simply the solution). The terms acidification and acidulation are used interchangeably in the entire specification.

The precipitation method of the invention is described in detail below. It contains some parts which also have been described above.

The inventors found that the addition of HCl to a magnesium salt of the carboxylic acid and subsequent precipitation of the carboxylic acid from the solution leads to a very efficient isolation of the carboxylic acid from a magnesium carboxylate solution.

In particular, it was found that succinic acid could be precipitated from a carboxylate solution acidified with HCl with a very high efficiency. Without wishing to be bound by any theory, the inventors expect that the high efficiency of the precipitation is due to a particular high salting out effect of $MgCl_2$ in the solution. This effect can be attributed to a decrease in solubility of the carboxylic acid due to the formation of $MgCl_2$ when the magnesium salt solution is acidified with HCl. In particular, the salting out effect is expected to be caused by the specific combination of HCl, magnesium and carboxylic acid. Since salting out effects are generally hard to predict, the particular high salting out effect observed in the precipitation method of the invention came as a surprise to the inventors.

Thus, using the precipitation method of the invention, a carboxylic acid precipitate can be obtained in a high yield from a magnesium carboxylate solution, which solution is for example a fermentation mixture obtained in a fermentation process. Furthermore, the obtained carboxylic acid precipitate has a relatively high purity, since the precipitation step in the precipitation method of the invention does not result in precipitation of large amounts of compounds other than carboxylic acid. Furthermore, a magnesium chloride solution is obtained, which is processed by way of a thermal decomposition step.

Furthermore, the specific choice for HCl and magnesium carboxylate provide for a reduction in salt waste and auxiliary materials needed in acidulation, in particular when, in accordance with the invention, combined with a thermal decomposition step of which the resulting HCl is re-used in the acidulation step.

The term "precipitating" as used herein refers to the formation of solid material starting from a fully dissolved state. Carboxylic acid can be precipitated in crystalline form or in amorphous form. By precipitating carboxylic acid according to the precipitation method of the invention, the carboxylic acid may also be purified. In case the magnesium carboxylate solution comprises dissolved impurities, precipitation of carboxylic acid typically separates the carboxylic acid from such impurities.

The term "solution to be precipitated" as used herein refers to the solution that is to be subjected to precipitation. Typically, this term refers to the solution comprising carboxylic acid and $MgCl_2$ obtained after acidulation, optionally after this solution has been subjected to a concentration step and/or a step wherein extra $MgCl_2$ is added. However, in case of a second or further precipitation step, the term "solution to be precipitated" refers to the $MgCl_2$ solution obtained after the latest precipitation step, optionally after this solution has been subjected to a concentration step and/or a step wherein extra $MgCl_2$ is added. Such $MgCl_2$ solutions may still comprise carboxylic acid, which may be obtained by subjecting it to a second or further precipitation step.

In the precipitation method, any magnesium carboxylate can be used, which in acidified form (i.e. wherein the corresponding carboxylic acid) has a solubility in water close to or lower than $MgCl_2$. Consequently, the carboxylic acid to be precipitated in the precipitation method of the invention has a solubility in water of 60 g/100 g water or less at 20° C. Carboxylic acids having a solubility in water considerably higher than $MgCl_2$ are not suitable to be precipitated with the precipitation method of the invention, because in this case large amounts of $MgCl_2$ will precipitate when precipitating the carboxylic acid, such that no suitable separation is obtained.

Preferably, the carboxylic acid corresponding with the carboxylate has a solubility that is lower than that of $MgCl_2$, as measured in water at 20° C., i.e. has a solubility in water of less than 54.5 g/100 g water at 20° C. (anhydrate). More preferably, the carboxylic acid has a solubility that is considerably lower than $MgCl_2$, such that $MgCl_2$ does not precipitate together with the carboxylic acid from the solution in the precipitation step. Therefore, the carboxylic acid preferably has a solubility in water at 20° C. of less than 30 g/100 g water, more preferably less than 15 g/100 g water, even more preferably less than 10 g/100 g water.

In one embodiment, the carboxylic acid to be precipitated with the precipitation method of the invention may be selected from the group consisting of succinic acid, itaconic acid, citric acid and fumaric acid. The carboxylic acid to be precipitated may also be adipic acid. The carboxylic acid is preferably succinic acid, because a particularly suitable salting out effect was observed for this specific acid. Succinic acid has a solubility of 6.75 g/100 g water at 20° C.

Accordingly, the magnesium carboxylate may be selected from the group consisting of magnesium succinate, magnesium itaconate, magnesium fumarate, magnesium citrate and magnesium adipate.

The magnesium carboxylate provided in the precipitation method of the invention may be obtained in a fermentation process.

The magnesium carboxylate may be provided in solid (e.g. crystalline) form. Alternatively, the magnesium carboxylate may be in dissolved form, for example as part of a solution or suspension. Such a solution or suspension comprising dissolved magnesium carboxylate may be aqueous and may in particular be obtained in a fermentation process. An example of a suspension may for example be a suspension comprising dissolved magnesium carboxylate and insoluble biomass, such as a fermentation broth.

For practical reasons, the upper limit of the magnesium carboxylate concentration may be 20 wt. %, for example in case of the magnesium carboxylate being succinate. In case of succinate, concentrations higher than 20 wt. % require the solution to have a temperature of 75° C., which is bad for the equipment due to the presence of HCl.

To yield as much carboxylic acid as possible after acidulation and precipitation, the carboxylate concentration going into the acidulation is preferably as high as possible. In case the magnesium carboxylate is provided as a solution, the upper limit of the magnesium carboxylate concentration is determined by the solubility of the magnesium carboxylate. In case the carboxylate is provided as a suspension, the stirrability of the suspension typically determine the upper limit. In case the carboxylate is provided as a solid cake, the solid liquid separation and resulting adhering water typically determine the upper limit. The combination of the above mentioned input concentration must favorably result in a situation where $MgCl_2$ remains in solution and as much as possible carboxylic acid precipitates during the precipitation step.

In case a magnesium carboxylate solution or suspension is obtained from a fermentation process which does not have a sufficiently high magnesium carboxylate concentration, the solution may be concentrated, for example by evaporation.

The precipitation method of the invention comprises an acidulation step, wherein the magnesium carboxylate is acidified with gaseous HCl, thereby obtaining a solution comprising carboxylic acid and $MgCl_2$. This step is described in detail above.

Acidulation is typically conducted using an excess of HCl. The excess is preferably small, such that the $MgCl_2$ solution obtained after precipitation is not highly acidic, which may not be desirable in view of further processing such a solution. For example, the excess of HCl used may be such that the resulting $MgCl_2$ solution after precipitation has a pH of 1 or higher, such as a pH of about 1.5.

The precipitation method of the invention may comprise a concentration step, wherein the solution obtained after acidulation with HCl is concentrated. A higher concentration of carboxylic acid in the solution will increase the efficiency of the carboxylic acid precipitation. The concentration step may be conducted by evaporation.

The precipitation method of the invention further comprises precipitating the carboxylic acid from the solution obtained in the acidulation step or, if present, from the solution obtained in the concentration step. This step may be referred to as the (first) precipitation step. Precipitation may be conducted by any precipitation method known in the art, such as reactive precipitation or by cooling, concentrating, evaporating the solution to be precipitated or by adding an antisolvent to the solution to be precipitated.

Precipitation is established by acidifying the magnesium carboxylate with HCl may be referred to as reactive precipitation. In reactive precipitation, precipitation takes place during acidulation. Consequently, acidifying the magnesium carboxylate and precipitating the thus obtained carboxylic acid are conducted as one step. Accordingly, in a preferred embodiment, the precipitation method of the invention comprises only the steps of providing magnesium carboxylate obtained in a fermentation process (as described above); and acidifying the magnesium carboxylate with HCl as described above, thereby obtaining a carboxylic acid precipitate and a $MgCl_2$ solution. The precipitation step thus may result in a suspension with the carboxylic acid precipitate present in the $MgCl_2$ solution.

Reactive precipitation can be conducted by choosing, the conditions in the acidulation step such that immediate precipitation of the carboxylic acid can occur. The skilled person will know how to establish such conditions. In particular, the magnesium carboxylate concentration may be chosen such that the acidulation with HCl will result in a carboxylic acid concentration that is higher than the saturation concentration of the carboxylic acid.

The precipitation step may also be conducted by cooling the solution to be precipitated, e.g. the solution formed in the acidulation step, or, if present, from the solution obtained in the concentration step. This type of precipitation may be referred to as cooling precipitation. The cooling step may require that the solution to be precipitated is first heated to a temperature at which substantially all $MgCl_2$ and carboxylic acid are dissolved. The solution to be precipitated may be cooled from a temperature above the nucleation temperature of the carboxylic acid in the solution to a temperature below the nucleation temperature of the carboxylic acid in the solution. The nucleation temperature is the highest temperature at which solids, in particular, precipitate, is formed. This temperature is i.a. dependent on the concentration of $MgCl_2$, carboxylic acid and the presence of other components. Therefore, it is not possible to give a single temperature value for the nucleation temperature. However, in general, the solution to be precipitated is cooled from a temperature of at least 35° C. to a temperature of less than 30° C., preferably at least 40° C. to a temperature of less than 25° C. In case of a cooling precipitation the carboxylic acid concentration prior to cooling is preferably as close to the solubility as is economically feasible. The carboxylic acid concentration may for example be 0-100 g/L or lower (or 0-50 g/L or lower) than the solubility of the carboxylic acid.

Furthermore, precipitation may be established by concentrating the solution comprising the carboxylic acid and $MgCl_2$, preferably by evaporation. Evaporation of part of the solvent of the solution comprising the carboxylic acid and $MgCl_2$ will result in a higher concentration of the carboxylic acid and a stronger salting out effect, which enhances precipitation.

Furthermore, precipitation may be established by adding an antisolvent to the solution to be precipitated. Antisolvents are miscible with or soluble in the solution to be precipitated. Examples of antisolvents are alcohols, in particular C1-C3 alcohols, e.g., methanol, ethers, in particular C2-ethers, e.g. dimethylether, and ketones, in particular C2-C4 ketones, e.g., acetone.

Preferably, the $MgCl_2$ solution obtained after precipitation may be subjected to a second and/or further precipitation step, thereby forming additional carboxylic acid precipitate and a second and/or further $MgCl_2$ solution. The second or further precipitation step may be conducted to recover at least part of the carboxylic acid remaining in the $MgCl_2$ solution obtained in the previous precipitation step. In this case, the precipitation step of the invention may be referred to as the first precipitation step. The $MgCl_2$ solution obtained in the first precipitation of the precipitation method may still comprise small amounts of carboxylic acid. To recover at least part of this carboxylic acid, a second precipitation step may be conducted. Such a second precipitation step may be conducted under similar conditions as the first precipitation step, including a concentration step and/or the addition of $MgCl_2$ conducted prior to the precipitation step.

In a preferred embodiment, the precipitation method of the invention comprises a first precipitation reaction, which is a reactive precipitation step, after which the $MgCl_2$ solution obtained in this step is subjected to a cooling and/or evaporation step. The cooling and/or evaporation step are further precipitation steps, wherein additional carboxylic acid is precipitated.

Prior to any precipitation step, magnesium chloride may be added to the solution to be precipitated. This solution may be the solution comprising the magnesium carboxylate (in case of reactive precipitation) or to the solution comprising carboxylic acid and magnesium chloride (as obtained in the acidulation step). Such added magnesium chloride may increase the salting out effect, thereby enhancing the precipitation of carboxylic acid.

In one embodiment, the magnesium carboxylate provided in the precipitation method of the invention is obtained in a fermentation process. In such a fermentation process a carbohydrate source is typically fermented by means of a microorganism to form a carboxylic acid. Subsequently, a magnesium base is added as neutralising agent during fermentation to provide the magnesium salt of the carboxylic acid. Examples of suitable magnesium bases are magnesium hydroxide $(Mg(OH)_2)$, magnesium carbonate $(MgCO_3)$ and magnesium bicarbonate $(Mg(HCO_3)_2)$. The advantage of the use of $Mg(OH)_2$ as a base is that this compound can be provided by the precipitation method of the invention. The use of $MgCO_3$ may also desirable and can be easily obtained by converting $Mg(OH)_2$ obtained in the precipitation method of the invention. Furthermore, the use of $MgCO_3$ or $Mg(OH)_2$ is desirable, because hydroxide and carbonate are not expected to have a negative effect on the salting out effect of the precipitation method of the invention (any carbonate left after neutralising may leave the solution as gaseous $CO_2$).

The fermentation process may comprise a purification step, wherein the magnesium carboxylate is crystallised from the fermentation broth, which may then be subsequently dissolved in water to form an aqueous solution, which typically has a higher concentration of carboxylate than the fermentation broth. Such a purification step may have the advantage that a higher yield can be obtained in the first precipitation step due to the higher concentration of the magnesium carboxylate, in particular when the carboxylate is succinate.

The crystallisation may comprise at least one of a concentration step, such as a water evaporation step, a cooling step, a seeding step, a separation step, a washing step and a re-crystallisation step. Concentration may be performed as a separate step or together with crystallisation (e.g. evaporative-crystallisation).

In one embodiment the present invention pertains to an integrated process comprising the steps of
   subjecting a carbon source to a fermentation step to form a carboxylic acid, which fermentation step comprises the steps of fermenting a carbon source by means of a microorganism in a fermentation broth to form carboxylic acid and neutralizing at least part of the carboxylic acid by adding a magnesium base selected from magnesium oxide and magnesium hydroxide, thereby obtaining a magnesium carboxylate,
   subjecting the magnesium carboxylate to an acidification step wherein the magnesium carboxylate is contacted with a gas stream comprising gaseous HCl to form a liquid effluent comprising carboxylic acid and magnesium chloride,
   subjecting the liquid effluent comprising carboxylic acid and magnesium chloride to a separation step to yield a carboxylic acid and a liquid comprising magnesium chloride,
   subjecting the aqueous liquid comprising magnesium chloride to a temperature of at least 300° C., thereby decomposing magnesium chloride into magnesium oxide and hydrogen chloride, thus obtaining a solid comprising magnesium oxide and a gas comprising gaseous hydrogen chloride, which gas is provided to the acidification step,
   providing the magnesium oxide as neutralising agent to the fermentation step, either as such or after conversion to magnesium hydroxide.

In one embodiment, a concentration step is carried out after the fermentation step and before the acidification step, resulting in a liquid feed with a temperature of at least 60° C.

The various steps of the process according to this embodiment of the invention may be carried out as described in more detail above.

It will be evident to the skilled person that the various aspects of the present invention which are described above in different paragraphs may be combined.

The invention and certain embodiments of the inventions are illustrated by the following examples and/or embodiments, without being limited thereto or thereby.

EXAMPLE 1

Preparation Gaseous HCl Stream

A gaseous HCl containing stream (the gas feed) was prepared by evaporating 765 g/hr of a 18 wt % solution of HCl in water into a 930 g/hr pre-heated gaseous nitrogen stream at a temperature of 95° C. This gaseous HCl stream is meant to resemble a gaseous HCl stream obtained by thermohydrolysis of a 25-30 wt % magnesium chloride solution in water. The thus prepared gaseous HCl stream comprised 8 wt % of HCl, 37 wt % of water and 55 wt % of nitrogen.

Although gaseous HCl streams obtained in a thermohydrolysis process typically comprise additional compounds, in particular other gases such as oxygen and carbon dioxide and impurities such as volatile carboxylic acids, the gaseous HCl stream prepared in this example is considered to sufficiently resemble such gaseous HCl streams such that the proof of principle shown in Examples 2-6 using this gas equally applies to gaseous HCl streams obtained in a thermohydrolysis process.

EXAMPLE 2

Absorption with Water and Separate Acidulation—Comparative

In this experiment, the gaseous HCl stream of Example 1 was absorbed in water to obtain a HCl containing solution, which solution was used to acidify a magnesium succinate solution. Absorption of the gaseous HCl stream in water was conducted in an insulated glass column with a length of 1.1 m and 45 mm internal diameter. The active absorption section of the column (95 cm) was equipped with glass Raschig rings with a diameter of 4 mm and height of 4 mm. The internal temperature of the column was measured and controlled to maintain a temperature of 95° C. Demineralised water was introduced in the top and the gaseous HCl stream at the bottom of the column. The column was operated with the gaseous HCl stream as a continuous phase and demineralised water flowing over the Raschig rings. The interface level in the bottom of the column was observed visually and controlled via a manually operated valve in the acidulated aqueous stream leaving the bottom of the column. The depleted gaseous HCl stream was allowed to leave the top of column.

The gaseous HCl stream (1695 g/hr, 95° C.) used was prepared according to Example 1. It was contacted counter currently in the absorption setup described above with demineralised water (825 g/hr) at a temperature of 95° C. Samples were taken from the aqueous bottom phase. The concentration of HCl in this sample was determined to be 18 wt %.

The resulting HCl containing solution was subsequently used to acidulate a 20 wt % magnesium succinate solution. This magnesium succinate feed solution (aqueous mixture) was prepared by adding magnesium hydroxide (58 g) to a solution of 118 g succinic acid in 664 g water and stirred up to complete dissolution. This solution was meant to resemble a magnesium succinate solution obtained in a fermentation process. Although a magnesium succinate solution obtained in a fermentation process generally comprises compounds other than magnesium succinate, such as a relatively large amount of impurities, the magnesium succinate solution prepared for this example was considered to sufficiently resemble such a succinate solution obtained in a fermentation process to show the proof of principle that the invention works.

Subsequently, 100 g of the prepared magnesium succinate solution was acidulated by adding 60 g of the HCl containing solution (18 wt %) at a temperature of 95° C. The composition of the acidulated mixture was determined and was found to contain 11 wt % succinic acid, 8 wt % of magnesium chloride and <0.5 wt % HCl.

This example shows that by separate absorption with water followed by acidulation an acidulated product mixture is obtained that contains 11 wt % succinic acid and 8 wt % of magnesium chloride dissolved in water. Complete removal of the succinic acid product would yield a solution of 9 wt % magnesium chloride in water. Thus, if this solution would be fed to a thermohydrolysis process, 10 kg of water would need to be evaporated for each kg of magnesium chloride.

EXAMPLE 3

Integrated Absorption/Acidulation with Liquid Magnesium Carboxylate Feed

In this example, a gaseous HCl stream prepared according to Example 1 was absorbed directly in a magnesium succinate solution, thereby acidifying succinate into succinic acid and further obtaining magnesium chloride.

A gaseous HCl stream (1695 g/hr, 95° C.) prepared according to Example 1 was contacted counter currently in the absorption setup described in Example 2 with the 20 wt % magnesium succinate solution prepared according to the description in Example 2 (1320 g/hr) at a temperature of 95° C. Thus, the absorption step described in Example 2 was effectively repeated using the magnesium succinate feed solution instead of demineralised water. Samples were taken from the aqueous bottom phase and analyzed. The composition of the acidulated mixture was determined to be 15 wt % succinic acid, 12 wt % of magnesium chloride and <0.5 wt % HCl.

This example shows that by integrated absorption and acidulation an acidulated product mixture is obtained that contains 15 wt % succinic acid and 12 wt % of magnesium chloride dissolved in water. Complete removal of the succinic acid product would yield a solution of 14 wt % magnesium chloride in water. Thus, if this solution would be fed to a thermohydrolysis process, 6 kg of water would need to be evaporated for each kg of magnesium chloride, which is only 60% the amount of water that would have been needed in example 2.

EXAMPLE 4

Integrated Absorption/Acidulation with Increased Temperature Liquid Magnesium Carboxylate Feed Example 3 was repeated, but instead of a magnesium succinate solution having a temperature of 95° C., a magnesium succinate having a temperature of 120° C. was used. Samples were taken from the aqueous bottom phase and analyzed. The composition of the acidulated mixture was determined to be 16 wt % succinic acid, 13 wt % of magnesium chloride and <0.5 wt % HCl. This example shows that by increasing the feed temperature of the magnesium carboxylate liquid feed the concentrations in the acidulated product mixture are increased to 16 wt % succinic acid and 13 wt % of magnesium chloride dissolved in water compared to example 3. Complete removal of the succinic acid product would yield a solution of 16 wt % magnesium chloride in water. Thus, if this solution would be fed to a thermohydrolysis process, 5 kg of water would needs to be evaporated for each kg of magnesium chloride, which is less water compared to example 3.

EXAMPLE 5

Integrated Absorption/Acidulation with Magnesium Carboxylate Slurry Feed

Example 3 was repeated, but instead of using the 20 wt. % magnesium carboxylate solution (1320 g/hr), a 29 wt. % magnesium lactate slurry (1310 g/hr) was used. The 29 wt % magnesium lactate is equivalent to 20 wt % magnesium succinate in terms of carboxylate groups per unit weight. The magnesium lactate feed slurry was prepared by adding magnesium hydroxide (116 g) to a solution of 360 g lactic acid in 1948 g water. This solution was meant to resemble a magnesium lactate slurry obtained in a fermentation process. Although solutions obtained in a fermentation process typically comprise additional compounds, in particular impurities such as sugars, protein and/or biomass, the feed solution prepared in this example is considered to sufficiently resemble such solutions such that the proof of principle shown in this Example equally applies to feed solutions obtained in a fermentation process.

Samples were taken from the aqueous bottom phase and analyzed. The composition of the acidulated mixture was determined to be 23 wt % lactic acid, 12 wt % of magnesium chloride and <0.5 wt % HCl.

This example shows that integrated absorption and acidulation can also be performed with a carboxylate slurry feed and that an acidulated product mixture is obtained that contains 23 wt % lactic acid and 12 wt % of magnesium chloride dissolved in water. Complete removal of the lactic acid product would yield a solution of 16 wt % magnesium chloride in water. Thus, if this solution would be fed to a thermohydrolysis process, 5 kg of water would need to be evaporated for each kg of magnesium chloride.

The invention claimed is:

1. A method for preparing a carboxylic acid by acidification of a liquid feed comprising a carboxylate salt, which method comprises the steps of
providing a liquid feed comprising magnesium carboxylate;
providing a gas feed comprising gaseous hydrogen chloride; and
acidifying the carboxylate to carboxylic acid by bringing the liquid feed into contact with the gas feed, thereby forming a liquid effluent comprising carboxylic acid and magnesium chloride,
wherein the gas feed comprising gaseous hydrogen chloride is derived from a thermal decomposition step wherein an aqueous liquid comprising magnesium chloride is subjected to a temperature of at least 300° C., thereby decomposing magnesium chloride into magnesium oxide and hydrogen chloride, thus obtaining a solid comprising magnesium oxide and a gas comprising gaseous hydrogen chloride.

2. The method according to claim 1, wherein the gas feed comprises gaseous hydrogen chloride and gaseous water.

3. The method according to claim 2, wherein the hydrogen chloride to water weight ratio in the gas feed is between 1:10 and 1:4.

4. The method according to claim 1, further comprising a separation step, wherein the carboxylic acid and chloride salt present in the liquid effluent are separated from each other, thereby obtaining a carboxylic acid product stream and a magnesium chloride solution or suspension, wherein the magnesium chloride solution or suspension is provided as liquid comprising magnesium chloride to the thermal decomposition step.

5. The method according to claim 4 wherein the separation step comprises an extraction step or a precipitation step.

6. The method according to claim 1, wherein the liquid feed has a temperature of 20-50° C.

7. The method according to claim 1, wherein the liquid feed has a temperature of 80-120° C. under atmospheric pressure.

8. The method according to claim 1, wherein the temperature of the liquid feed is 1-50° C.

9. The method according to claim 1, wherein the gas feed further comprises at least 25 wt. % inert gas.

10. The method according to claim 1, wherein the feed gas comprises at least 2 wt. % hydrogen chloride.

11. The method according to claim 1, wherein the carboxylate is selected from the group consisting of lactate, succinate, propionate, 3-hydroxypropionate, hydroxybutyrate, citrate, fumarate, itaconate, adipate, acrylate, levulinate, maleate, 2,5-furandicarboxylate, fatty acylate and a lactylate and/or mixtures hereof, preferably from the group consisting of lactate, succinate, propionate, 2,5-furandicarboxylate and 3-hydroxypropionate, in particular from the group of lactate and succinate.

12. The method according to claim 1, wherein the method further comprises the step of preparing the liquid feed by a fermentation step.

13. The method according to claim 11, wherein a concentration step is carried out after the fermentation step and before the acidification step, resulting in a liquid feed with a temperature of at least 60° C.

14. The method according to claim 1, which is an integrated process comprising the steps of
subjecting a carbon source to a fermentation step to form a carboxylic acid, which fermentation step comprises the steps of fermenting a carbon source by means of a microorganism in a fermentation broth to form carboxylic acid and neutralizing at least part of the carboxylic acid by adding a magnesium base selected from magnesium oxide and magnesium hydroxide, thereby obtaining a magnesium carboxylate,
subjecting the magnesium carboxylate to an acidification step wherein the magnesium carboxylate is contacted with a gas stream comprising gaseous HCl to form a liquid effluent comprising carboxylic acid and magnesium chloride,
subjecting the liquid effluent comprising carboxylic acid and magnesium chloride to a separation step to yield a carboxylic acid and a liquid comprising magnesium chloride,
subjecting the aqueous liquid comprising magnesium chloride to a temperature of at least 300° C., thereby decomposing magnesium chloride into magnesium oxide and hydrogen chloride, thus obtaining a solid comprising magnesium oxide and a gas comprising gaseous hydrogen chloride, which gas is provided to the acidification step,
providing the magnesium oxide as neutralising agent to the fermentation step, either as such or after conversion to magnesium hydroxide.

15. The method according to claim 14, wherein a concentration step is carried out after the fermentation step and before the acidification step, resulting in a liquid feed with a temperature of at least 60° C.

* * * * *